United States Patent
He et al.

(10) Patent No.: US 11,628,168 B2
(45) Date of Patent: Apr. 18, 2023

(54) MEDICAL APPLICATION OF PYRIMIDINE SULFONAMIDES DERIVATIVES

(71) Applicants: CHINESE PLA GENERAL HOSPITAL, Beijing (CN); SHIJIAZHUANG SAGACITY NEW DRUG DEVELOPMENT COMPANY, LTD., Hebei (CN)

(72) Inventors: Kunlun He, Beijing (CN); Xiaojian Gao, Beijing (CN); Chunlei Liu, Beijing (CN); Zeyu Zhang, Beijing (CN); Xin Li, Beijing (CN); Chen Li, Beijing (CN); Yunfu Luo, Shanghai (CN); Maoyi Lei, Shanghai (CN); Junmiao Li, Shanghai (CN); Yiwei Wang, Shijiazhuang (CN)

(73) Assignees: CHINESE PLA GENERAL HOSPITAL, Beijing (CN); SHIJIAZHUANG SAGACITY NEW DRUG DEVELOPMENT COMPANY, LTD., Hebei (CN)

(*) Notice: Subject to any disclaimer, the term of this patent is extended or adjusted under 35 U.S.C. 154(b) by 1 day.

(21) Appl. No.: 17/279,525

(22) PCT Filed: Jun. 5, 2019

(86) PCT No.: PCT/CN2019/090109
§ 371 (c)(1),
(2) Date: Mar. 24, 2021

(87) PCT Pub. No.: WO2020/062912
PCT Pub. Date: Apr. 2, 2020

(65) Prior Publication Data
US 2021/0393627 A1    Dec. 23, 2021

(30) Foreign Application Priority Data

Sep. 25, 2018 (CN) .................. CN201811113581

(51) Int. Cl.
*A61K 31/506*    (2006.01)

(52) U.S. Cl.
CPC .................. *A61K 31/506* (2013.01)

(58) Field of Classification Search
None
See application file for complete search history.

(56) References Cited

FOREIGN PATENT DOCUMENTS

| CN | 1524079 A | 8/2004 |
|---|---|---|
| CN | 1711248 A | 12/2005 |

(Continued)

OTHER PUBLICATIONS

Bohli, M.H. The Discovery of N-[5-(4-Bromophenyl)-6-[2-[(5-bromo-2-pyrimidinyl)oxy]ethoxy]-4-pyrimidinyl]-N'-propylsulfamide (Macitentan), an Orally Active, Potent Dual Endothelin Receptor Antagonist. J. Med. Chem. 55, 7849-7861 (Year: 2012).*

(Continued)

*Primary Examiner* — Mark L Shibuya
*Assistant Examiner* — LuisAlberto Gonzalez
(74) *Attorney, Agent, or Firm* — AEON Law, PLLC; Adam L. K. Philipp; Shan Liao

(57) ABSTRACT

The present disclosure provides application of a compound in conformity with a general formula I and an isomer or pharmaceutically acceptable salt thereof to preparation of a medicinal composition for treating or preventing a high altitude disease. The high altitude disease is selected from an acute high altitude disease and a chronic high altitude disease generated in a high altitude environment with an altitude of 2,000 m or above.

11 Claims, 1 Drawing Sheet

(56) References Cited

FOREIGN PATENT DOCUMENTS

CN          109232546 A     1/2019
WO     WO-2019101039 A1 *   5/2019   ........... A61K 31/506

OTHER PUBLICATIONS

Machine translation of W02019101039A1, 49 pages (Year: 2019).*
Betge, Influence of Macitentan on the Vascular Tone and Recruitment of Capillaries under Hypobaric Hypoxia in High Altitude, European Heart Journal, vol. 38, Aug. 29, 2017, ISSN: 1522-9645, p. 279.
International Search Report of PCT/CN2019/090109.
Modesti, Role of Endothelin-1 in Exposure to High Altitude Acute Mountain Sickness and Endothelin-1 (ACME-1) Study, Circulation, vol. 114, Issue 13, Sep. 26, 2006, ISSN: 1524-4539, p. 1410-1416.
Neumanna, Retinal Vessel Regulation at High Altitudes1, Clinical Hemorheology and Microcirculation, vol. 63, Issue 3, Sep. 12, 2016, ISSN:1386-0291, p. 281-292.

* cited by examiner

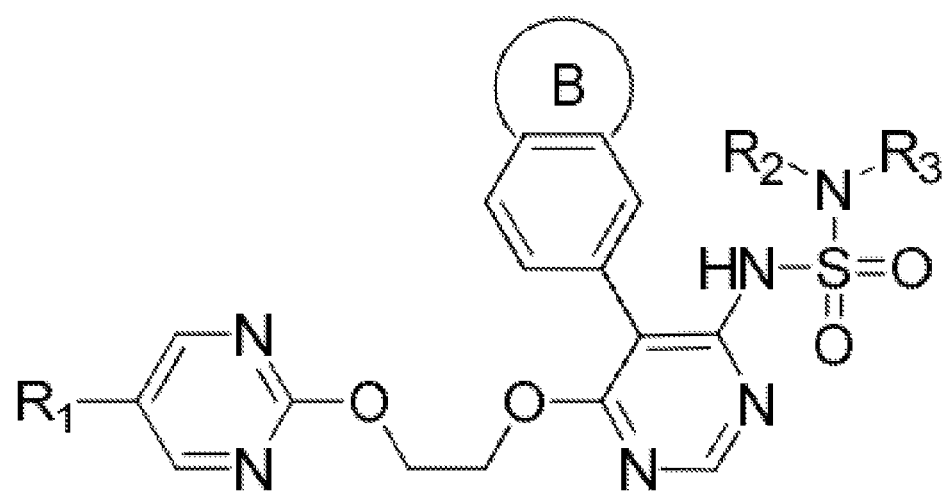

MEDICAL APPLICATION OF PYRIMIDINE SULFONAMIDES DERIVATIVES

RELATED APPLICATIONS

This application is a U.S. National Phase of PCT Patent Application No. PCT/CN2019/090109 having International filing date of Jun. 5, 2019, which claims the benefit of priority of a Chinese Patent Application No. CN201811113581.4, filed Sep. 25, 2018. The entire contents of the above-referenced applications and of all priority documents referenced in the Application Data Sheet filed herewith are hereby incorporated by reference for all purposes.

TECHNICAL FIELD

The present disclosure relates to the technical field of biological medicine, and particularly relates to application of pyrimidine sulfonamide derivatives to preparation of a medicinal composition for treating or preventing a high altitude disease.

BACKGROUND

High altitude sickness, i.e., a high altitude disease, is a natural physiological reaction generated by the body for adapting to changes of atmospheric pressure difference, low oxygen content, dry air and the like caused by altitude after a person reaches a certain altitude. Symptoms of the high altitude sickness generally include headache, palpitation, fatigue, chest stuffiness, shortness of breath, emesis, appetite decrease, twitch, confusion, cognitive ability plummet and the like. Physical signs include cardiac acceleration, deepening breath, mild abnormal blood pressure, face or limb edema, paro xymally cyanosis and the like. Currently, drugs such as root of kirilow rhodiola, GaoYuanning, American ginseng, radix salviae miltiorrhizae pills, Bufferin and the like or related health care products are mostly adopted to prevent and condition the high altitude sickness. For example, there are patents CN103829245A, CN103948896A, CN104274808A, CN104288262A, CN104288735A, CN104288476A, CN104721202A, CN104706771A, CN105168308A, CN105193839A and the like, but these drugs or foods have defects of slow response, many side effects and the like.

The inventor is amazed to find a type of pyrimidine sulfonamide derivative endothelin-1 receptor $ET_AR$ and $ET_BR$ dual-antagonist compounds which have remarkable curative effects in the aspect of treating or preventing the high altitude disease.

The patent WO2002/053557 discloses a novel sulfonamide compound and application thereof as an active ingredient to preparation of a medicinal composition for treating hypertension, ischemia, vasospasm, angina pectoris, cancers, migraine, asthma, hyperlipidemia or inflammatory diseases and the like. The patent CN102510719A discloses an endothelin receptor antagonist for prevention or treatment of brain metastases in combination with a cytotoxicity chemotherapeutant, radiotherapy or both of the cytotoxicity chemotherapeutant and the radiotherapy. However, application of a compound in conformity with a general formula I, and an isomer or pharmaceutically acceptable salt thereof to preparation of a medicinal composition for treating or preventing a high altitude disease, as provided by the present disclosure, is not disclosed.

SUMMARY

The present disclosure provides application of a compound in conformity with a general formula I, and an isomer or pharmaceutically acceptable salt thereof to preparation of a medicinal composition for treating or preventing a high altitude disease, and particularly provides application to effective inhibition of the vasoconstrictor effect caused by ET-1.

General formula I

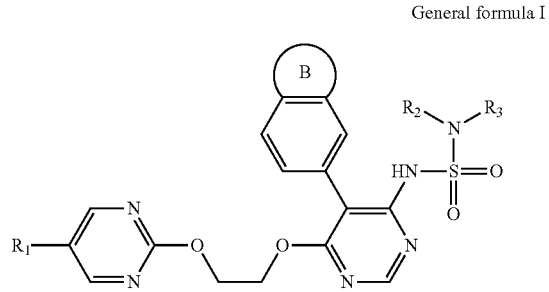

Wherein, $R_1$ is selected from H, F, Cl, Br, I, OH or $NH_2$;

$R_2$ is selected from H or $C_{1-3}$ alkyl, and the $C_{1-3}$ alkyl is optionally substituted with 1, 2 or 3 X;

$R_3$ is selected from H, $C_{1-6}$ alkyl, $C_{1-6}$ heteroalkyl, —$C_{1-3}$ alkyl-$C_{3-6}$ cycloalkyl, $C_{3-6}$ cycloalkyl and —$C_{1-3}$ alkyl-3- to 7-membered heterocycloalkyl, and the $C_{1-6}$ alkyl, the $C_{1-6}$ heteroalkyl, the —$C_{1-3}$ alkyl-$C_{3-6}$ cycloalkyl, the $C_{3-6}$ cycloalkyl or the —$C_{1-3}$ alkyl-3- to 7-membered heterocycloalkyl is optionally substituted with 1, 2 or 3 X; or, $R_2$ and $R_3$ are connected to form a 3- to 8-membered ring optionally substituted with 1, 2 or 3 X;

a ring B is selected from 3- to 7-membered heterocycloalkyl or 5-6-membered heteroaryl, and the 3- to 7-membered heterocycloalkyl or the 5-6-membered heteroaryl is optionally substituted with 1, 2 or 3 X;

X is respectively and independently selected from H, F, Cl, Br, I, OH, $NH_2$, CN, $C_{1-6}$ alkyl or $C_{1-6}$ heteroalkyl, and the $C_{1-6}$ alkyl or the $C_{1-6}$ heteroalkyl is optionally substituted with 1, 2 or 3 X';

X' is respectively and independently selected from F, Cl, Br, I, OH, $NH_2$, CN, Me, $CH_2F$, $CHF_2$, $CF_3$ and Et; and the $C_{1-6}$ heteroalkyl, the 3- to 7-membered heterocycloalkyl and the 5-6-membered heteroaryl each include 1, 2, 3 or 4 heteroatoms or heteroatom groups independently selected from N, —O—, —S—, —NH—, —S(=O)$_2$— or —S(=O)—.

Preferably, the X is selected from H, F, Cl, Br, I, OH, $NH_2$, CN, $C_{1-3}$ alkyl, $C_{1-3}$ alkyl-S(=O)$_2$— or $C_{1-3}$ alkyl-O—, and the $C_{1-3}$ alkyl, the $C_{1-3}$ alkyl-S(=O)$_2$— or the $C_{1-3}$ alkyl-O— is optionally substituted with 1, 2 or 3 X'.

Further preferably, the X is selected from H, F, Cl, Br, I, OH, $NH_2$, CN, Me, Et,

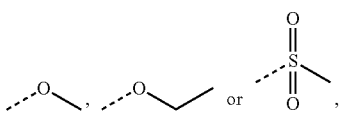

and the Me, Et,

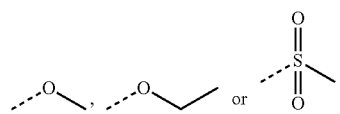

is optionally substituted with 1, 2 or 3 X'.

In one specific embodiment of the present disclosure, the X is selected from H, F, Cl, Br, I, OH, $NH_2$, CN, Me, $CH_2F$, $CHF_2$, $CF_3$, Et,

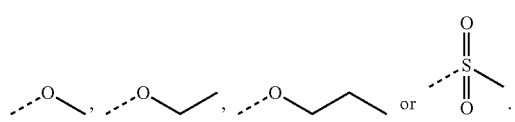

Preferably, the ring B is selected from tetrahydrofuryl, tetrahydrothienyl, 1,3-dioxolanyl, pyrrolidyl, thiazolyl, pyrazolyl or imidazolyl, and the tetrahydrofuryl, the tetrahydrothienyl, the 1,3-dioxolanyl, the pyrrolidyl, the thiazolyl, the pyrazolyl or the imidazolyl is optionally substituted with 1, 2 or 3 X.

Further preferably, the

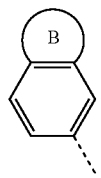

is selected from

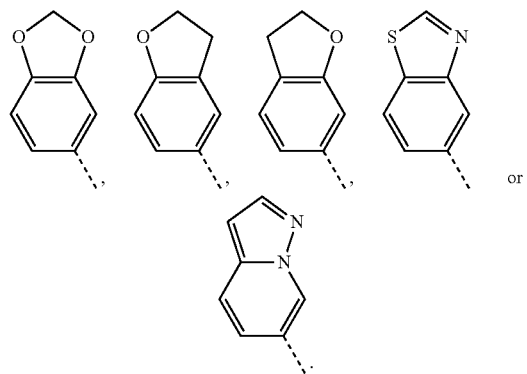

Preferably, the $R_2$ is selected from H or Me.

Preferably, the $R_3$ is selected from H, $C_{1-4}$ alkyl, $C_{1-4}$ alkyl-O—$C_{1-4}$ alkyl, cyclobutyl, —$C_{1-3}$ alkyl-cyclobutyl, —$C_{1-3}$ alkyl-cyclopropyl, —$C_{1-3}$ alkyl-tetrahydrofuryl and —$C_{1-3}$ alkyl-tetrahydropyranyl, and the $C_{1-4}$ alkyl, the $C_{1-4}$ alkyl-O—$C_{1-4}$ alkyl, the cyclobutyl, the —$C_{1-3}$ alkyl-cyclobutyl, the —$C_{1-3}$ alkyl-cyclopropyl, the —$C_{1-3}$ alkyl-tetrahydrofuryl or the —$C_{1-3}$ alkyl-tetrahydropyranyl is optionally substituted with 1, 2 or 3 X.

Further preferably, the $R_3$ is selected from H, Me, Et,

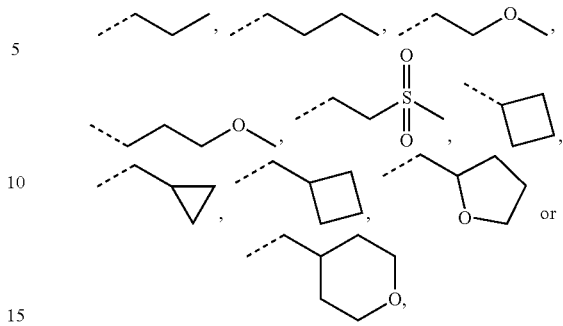

wherein the Me, Et,

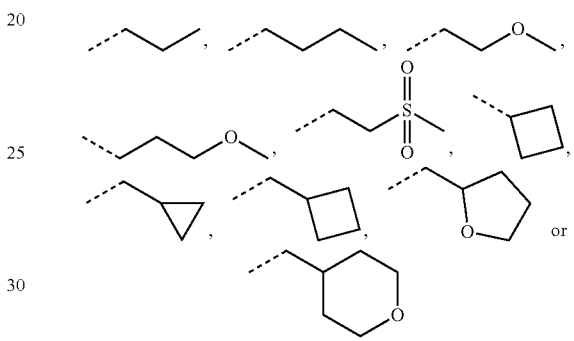

is optionally substituted with 1, 2 or 3 X.

In one specific embodiment of the present disclosure, the $R_3$ is selected from H, Me, ET,

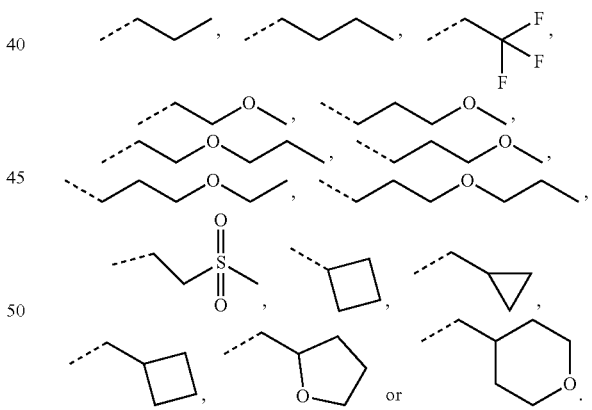

According to the present disclosure, the $R_2$ and the $R_3$ are connected to form 6- to 8-membered heterocycloalkyl, and the obtained 6- to 8-membered heterocycloalkyl is optionally substituted with 1, 2 or 3 X.

Preferably, the

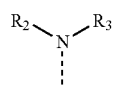

is selected from

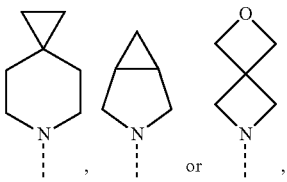, wherein the

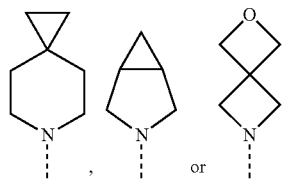, is optionally substituted with 1, 2 or 3 X.
Further preferably, the

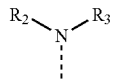

is selected from

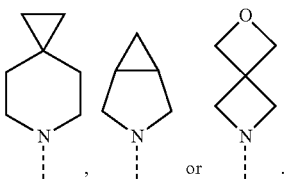.

Preferably, the $R_1$ is selected from H, F, Cl, Br, I, OH or $NH_2$; the X is selected from H, F, Cl, Br, I, OH, $NH_2$, CN, Me, $CH_2F$ $CHF_2$, $CF_3$, Et,

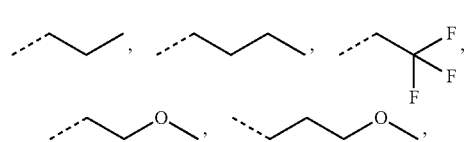

the ring B is selected from tetrahydrofuryl, tetrahydrothienyl, 1,3-dioxolanyl, pyrrolidyl, thiazolyl, pyrazolyl or imidazolyl, and the tetrahydrofuryl, the tetrahydrothienyl, the 1,3-dioxolanyl, the pyrrolidyl, the thiazolyl, the pyrazolyl or the imidazolyl is optionally substituted with 1, 2 or 3 X; the $R_2$ is selected from H or Me; and the $R_3$ is selected from H, Me, Et,

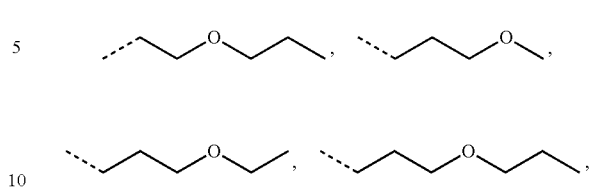

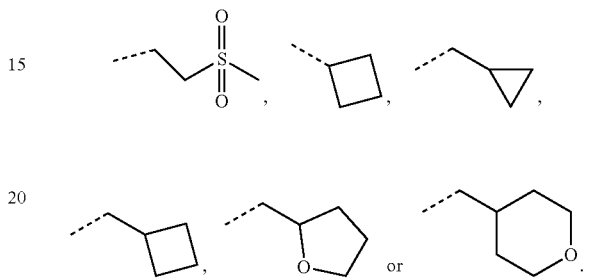

Further preferably, the $R_1$ is selected from F, Cl, Br or I; the

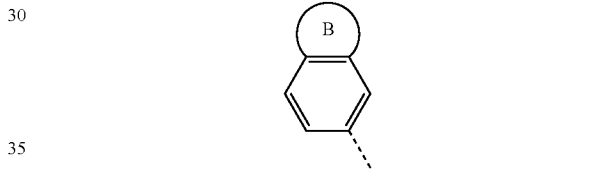

is selected from

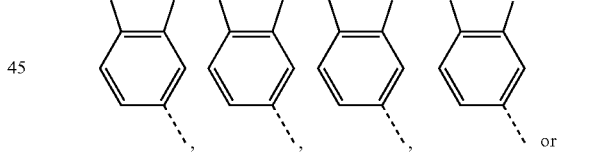;

the $R_2$ is H; and the $R_3$ is selected from

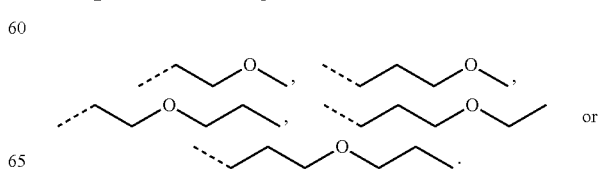

In one specific embodiment of the present disclosure, the compound in conformity with the general formula I is selected from one of the following:
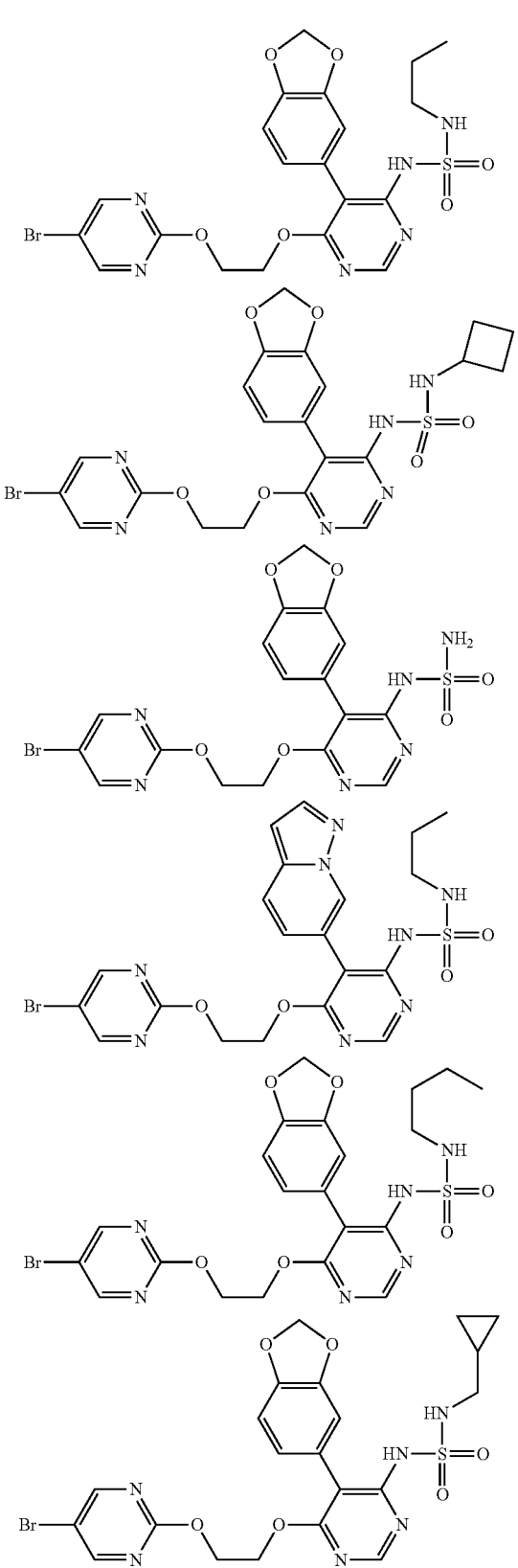
-continued
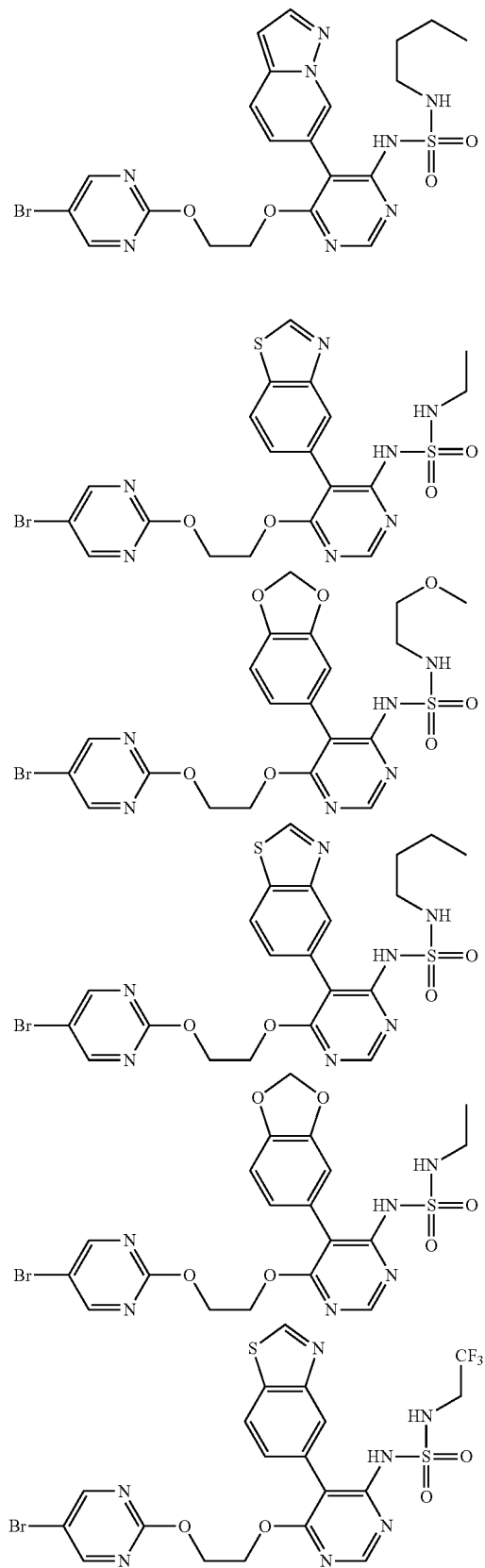

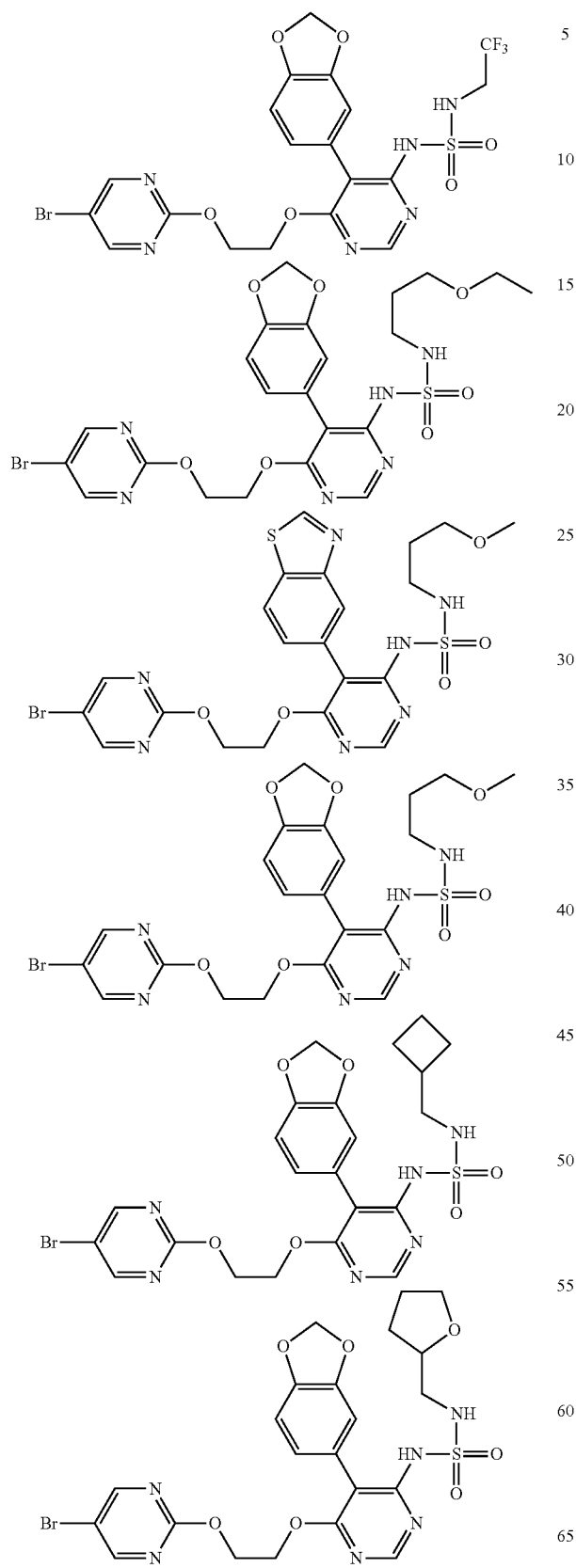
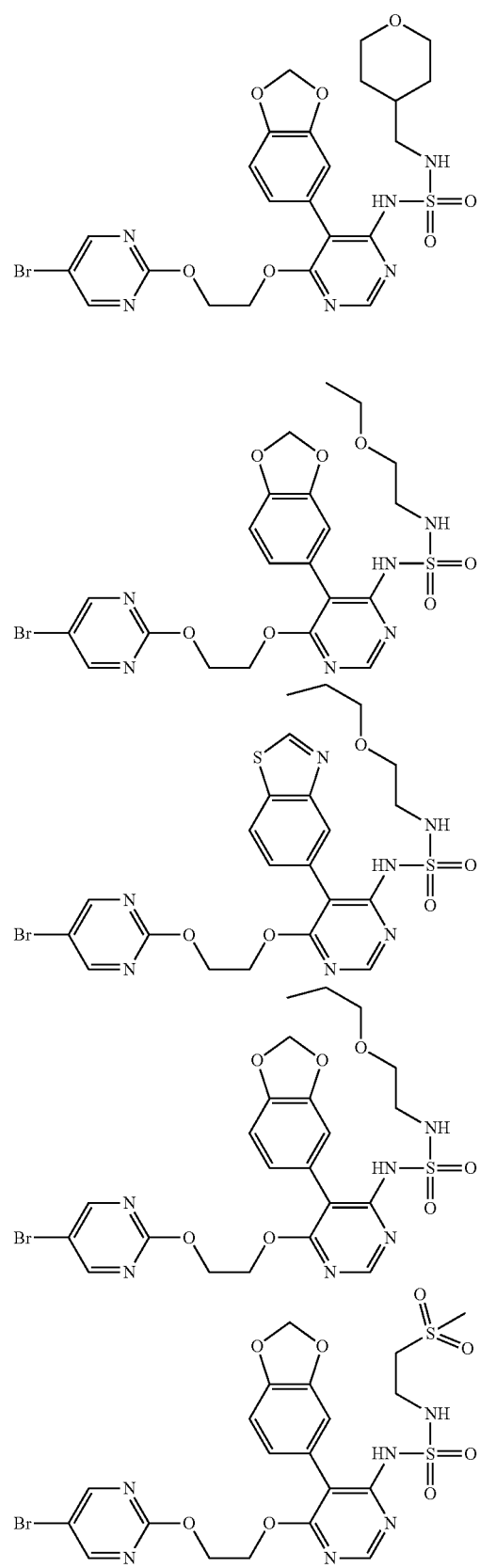

11
-continued
12
-continued
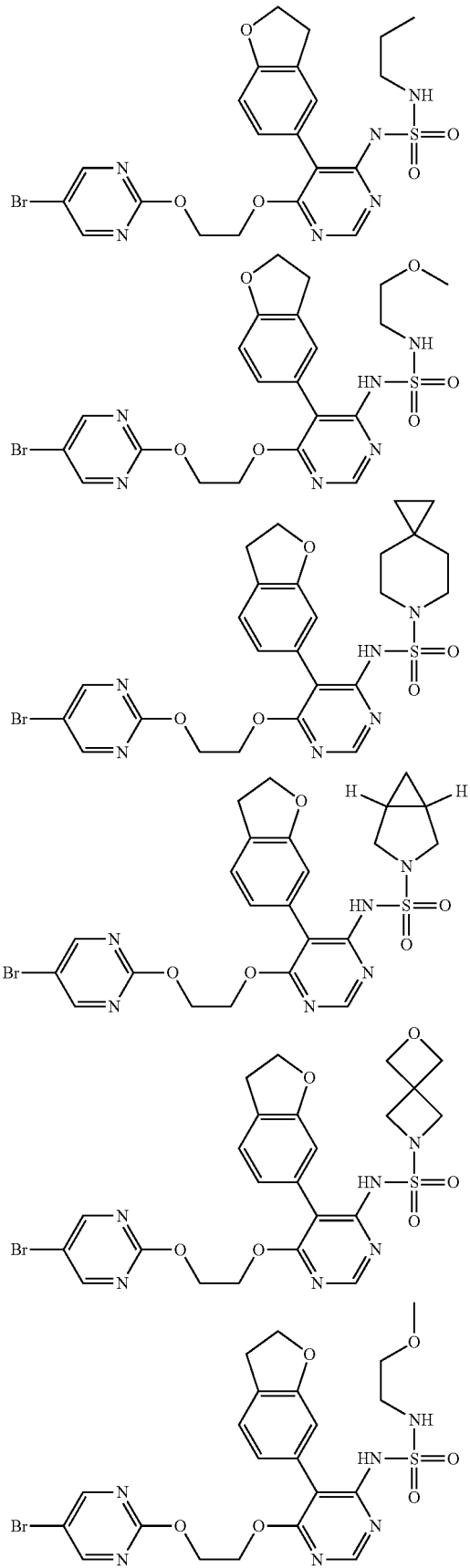
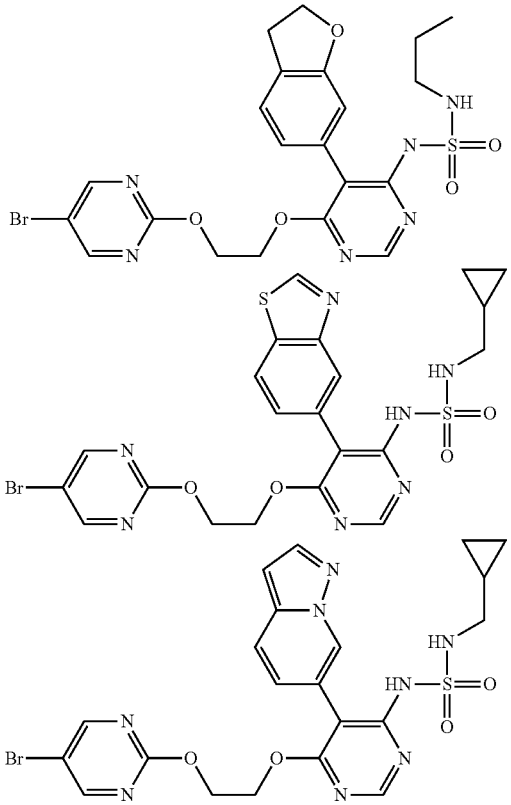
Preferably, in the compound in conformity with the general formula I, the $R_1$ is Br, the
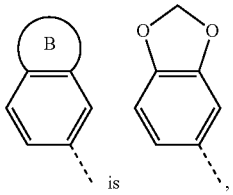
is
the $R_2$ is H, and the $R_3$ is
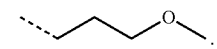
In one specific embodiment of the present disclosure, the compound as shown in the general formula I is SC0062, and a structural formula of the SC0062 is as follows:
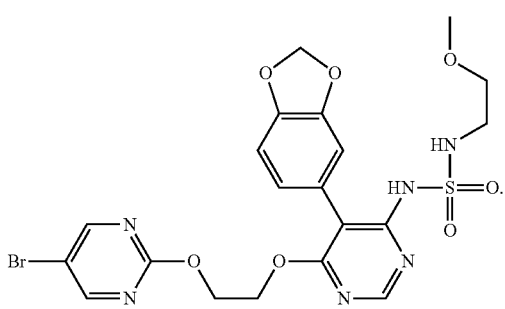

According to the present disclosure, the high altitude disease is selected from an acute high altitude disease and a chronic high altitude disease generated in a high altitude environment.

Preferably, the high altitude environment has an altitude of 2,000 m or above, and has conditions of low pressure and shortage of oxygen.

Further preferably, the high altitude environment has an altitude of 2,700 m or above, and has conditions of low pressure and shortage of oxygen.

In one specific embodiment of the present disclosure, the high altitude environment has an altitude of 5,500 m or above, and has conditions of low pressure and shortage of oxygen.

According to the present disclosure, the acute high altitude disease is selected from high altitude coma, high altitude cerebral edema, high altitude pulmonary edema or a mixed disease with coexistence of cerebral and pulmonary abnormality symptoms; and/or the chronic high altitude disease is selected from a high altitude heart disease, high altitude polycythemia, high altitude hypertension, high altitude hypotension or a mixed disease with coexistence of the heart disease and the polycythemia.

Preferably, the clinical manifestation of the high altitude disease is selected from one or a combination of two or more of headache, vertigo, palpitation, cardiac acceleration, fatigue, chest stuffiness, shortness of breath, deepening breath, nausea, emesis, insomnia, weakness, giddiness, somnolence, appetite decrease, twitch, confusion, numbness of hands and feet, paro xymally cyanosis, face edema, limb edema or cognitive ability plummet.

The present disclosure further provides application of a compound in conformity with the general formula I and an isomer or pharmaceutically acceptable salt thereof to preparation of a medicinal composition for protecting the cardio-pulmonary function in a high altitude environment.

According to the present disclosure, the protection on the cardio-pulmonary function is prevention or treatment on a cardio-pulmonary injury and/or a vascular injury in the high altitude environment. Preferably, the cardio-pulmonary injury and/or the vascular injury are pulmonary arterial hypertension and/or right ventricular hypertrophy.

According to the present disclosure, the medicinal composition includes the compound which is used as an active ingredient and has the general formula I, the isomer or the pharmaceutically acceptable salt of the compound, and a medicinal auxiliary material.

Preferably, the medicinal auxiliary material is selected from one or a combination of two or more of a solvent, an emulsifier, a plasticizer, a disintegrant, a filling agent, an adhesive, a sweetening agent or a lubricant.

According to the present disclosure, the solvent is selected from one or a combination of two or more of water, dichloromethane, hydroxypropyl-beta-cyclodextrin, polyethylene glycol-15-hydroxystearate, acetone or ethyl acetate. Preferably, the solvent is selected from one or a combination of two or more of the water, the hydroxypropyl-beta-cyclodextrin or the polyethylene glycol-15-hydroxystearate.

According to the present disclosure, the emulsifier is selected from one or a combination of two or more of polyethylene glycol oleate, polyvinyl alcohol, glyceryl stearate or tween-80. Preferably, the emulsifier is selected from one or a combination of the polyvinyl alcohol or the tween-80.

According to the present disclosure, the plasticizer is selected from one or a combination of two or more of polyethylene glycol, castor oil, glycerin or sorbitol. Preferably, the plasticizer is selected from one or a combination of the glycerin or the sorbitol.

According to the present disclosure, the disintegrant is selected from one or a combination of two or more of crosslinked povidone, sodium hydroxymethyl cellulose, sodium methyl cellulose starch or low-substituted hydroxypropyl cellulose. Preferably, the disintegrant is selected from one or a combination of the crosslinked povidone or the low-substituted hydroxypropyl cellulose.

According to the present disclosure, the filling agent is selected from one or a combination of two or more of microcrystalline cellulose, erythritol, sorbitol, mannitol, pregelatinized starch, calcium carbonate, sucrose or lactose. Preferably, the filling agent is selected from one or a combination of two or more of the microcrystalline cellulose, the calcium carbonate or the erythritol.

According to the present disclosure, the adhesive is selected from one or a combination of two or more of polyvinylpyrrolidone, carbomer, hydroxypropyl cellulose, gelatin, guar gum, sodium hydroxymethyl cellulose, hydroxypropyl methylcellulose, magnesium aluminosilicate, ethyl cellulose, hydroxyethyl cellulose, pregelatinized starch, Arabic gum, polyvinyl alcohol, povidone, maltodextrin or sodium alginate. Preferably, the adhesive is selected from one or a combination of two or more of the pregelatinized starch, the sodium hydroxymethyl cellulose, the maltodextrin or the polyvinylpyrrolidone.

According to the present disclosure, the sweetening agent is selected from one or a combination of two or more of aspartame, xylitol, menthol, peppermint essence, acesulfame potassium, steviol glycosides or sucralose. Preferably, the sweetening agent is selected from one or a combination of two or more of the steviol glycosides, the sucralose or the menthol.

According to the present disclosure, the lubricant is selected from one or a combination of two or more of talcum powder, hydrogenated calcium stearate, magnesium dodecyl sulfate, sodium stearyl fumarate, hydrated sodium silica gel, hydrogenated castor oil, zinc stearate or magnesium stearate. Preferably, the lubricant is selected from one or a combination of two or more of the sodium stearyl fumarate, the talcum powder or the hydrogenated calcium stearate.

Preferably, the medicinal composition is applied into a body in oral administration, intravenous or intraperitoneal ways.

In a specific embodiment of the present disclosure, the medicinal composition is applied into the body in the oral administration way.

Preferably, a dosage form of the medicinal composition is one or a combination of two or more of oral liquid, pills, granules, tablets or capsules.

The present disclosure further provides a preparation method of a medicinal composition including a compound with the general formula I and an isomer or pharmaceutically acceptable salt thereof. The preparation method includes the steps of: 1, uniformly dispersing the compound with the general formula I and the isomer or the pharmaceutically acceptable salt thereof into a medicinal auxiliary material; and 2, mixing and pressing into tablets and granules, filling the granules into capsule shells to prepare capsules, and after hot melting, dropwise adding the obtained product into condensate liquid to prepare dropping pills.

The present disclosure further provides application of a compound in conformity with the general formula I and an isomer or pharmaceutically acceptable salt thereof to preparation of a medicinal composition for protecting the cardiopulmonary function of a rat in a high altitude environment with an altitude of 5,500 m.

According to the present disclosure, the "alkyl" represents a straight-chain or branched-chain saturated hydrocarbon group, and may be monosubstituted (e.g., —$CH_2F$) or polysubstituted (e.g., —$CF_3$), and may be univalent (e.g., methyl), bivalent (e.g., methylene) or multivalent (e.g., methine). Preferably, the alkyl is $C_{1-20}$ alkyl. The $C_{1-20}$ alkyl is selected from methyl, ethyl, propyl, isopropyl, n-butyl, sec-butyl, isobutyl, tertiary butyl, 2-ethyl butyl, n-amyl, isoamyl, 1-methyl amyl, 1,3-dimethyl butyl, n-hexyl, 1-methyl hexyl, n-heptyl, isoheptyl, 1,1,3,3-tetramethyl butyl, 1-methyl heptyl, 3-methyl heptyl, n-octyl, 2-ethyl hexyl, 1,1,3-trimethyl hexyl, 1,1,3,3-tetramethyl amyl, nonyl, decyl, undecyl, 1-methyl undecyl, dodecyl, 1,1,3,3, 5,5-hexamethyl hexyl, tridecyl, tetradecyl, pentadecyl, cetyl, heptadecyl, octadecyl and eicosyl. Further preferably, the alkyl is $C_{1-6}$ alkyl, and includes, but is not limited to, methyl (Me), ethyl (Et), propyl (including n-propyl and isopropyl), butyl (including n-butyl, isobutyl, 5-butyl and b-butyl), amyl (including n-amyl, isoamyl and neo-amyl) and hexyl.

According to the present disclosure, the "heteroalkyl" represents a stable straight-chain or branched-chain alkyl atom group or a composition thereof, which includes a certain number of carbon atoms and at least one heteroatom or heteroatom group. The heteroatom is selected from B, O, N or S, wherein nitrogen and sulphur atoms are optionally oxidized, and a nitrogen heteroatom is optionally quaternized. Further preferably, the heteroatom group is selected from —C(=O)O—, —C(=O)—, —C(=S)—, —S(=O), —S(=O)$_2$—, —C(=O)N(H)—, —N(H)—, —C(=NH)—, —S(=O)$_2$N(H)— or —S(=O)N(H)—. The heteroalkyl includes, but is not limited to —$OCH_3$, —$OCH_2CH_3$, —$OCH_2CH_2CH_3$, —$OCH_2(CH_3)_2$, —$CH_2$—$CH_2$—O—$CH_3$, —$NHCH_3$, —$N(CH_3)_2$, —$NHCH_2CH_3$, —$N(CH_3)(CH_2CH_3)$, —$CH_2$—$CH_2$—NH—$CH_3$, —$CH_2$—$CH_2$—N($CH_3$)—$CH_3$, —$SCH_3$, —$SCH_2CH_3$, —$SCH_2CH_2CH_3$, —$SCH_2(CH_3)_2$, —$CH_2$—$SCH_2$—$CH_3$, —$CH_2$—$CH_2$—$S(=O)$—$CH_3$, —$CH_2$—$CH_2$—$S(=O)_2$—$CH_3$, —CH=CHO—$CH_3$, —$CH_2$—CH=N—$OCH_3$ or —CH=CHN($CH_3$)—$CH_3$.

According to the present disclosure, the "ring" is substituted or unsubstituted cycloalkyl, heterocycloalkyl, cycloalkenyl, heterocycloalkenyl, cycloalkynyl, heterocycloalkynyl, aryl or heteroaryl. The "ring" includes a monocyclic ring, a bicyclic ring, a spiro ring, a fused ring or a bridge ring. The "heterocyclic ring" is the monocyclic ring, a dicyclic ring or a tricyclic ring including a heteroatom or a heteroatom group, may be saturated, partially saturated or unsaturated (e.g., an aromatic system), the heteroatom or the heteroatom group includes atoms or an atom group except for carbon and hydrogen, e.g., oxygen (O), nitrogen (N), sulphur (S), silicon (Si), germanium (Ge), aluminium (Al), boron (B), —O—, —S—, =O, =S, —C(=O)O—, —C(=O)—, —C(=S)—, —S(=O), —S(=O)$_2$— and optionally substituted —C(=O)N(H)—, —N(H)—, —C(=NH)—, —S(=O)$_2$N(H)— or —S(=O)N(H)—.

According to the present disclosure, the "heterocycloalkyl" includes, but is not limited to, azetidinyl, oxetanyl, thietanyl, pyrrolidyl, pyrazolidyl, imidazolidinyl, tetrahydrothiophenyl, tetrahydrofuryl, tetrahydropyranyl, piperidyl, piperazinyl, morpholinyl, dioxanyl, dithianyl, isoxazolidinyl, isothiazolidinyl, 1,2-oxazinyl, 1,2-thiazinyl, hexahydropyridazinyl, homopiperazinyl, homopiperidinyl or oxepanyl.

According to the present disclosure, the "cycloalkyl" includes any stable cyclic or polycyclic alkyl, and any carbon atoms are all saturated, may be monosubstituted or polysubstituted and may be univalent, divalent or multivalent. The cycloalkyl includes, but is not limited to, cyclopropyl, norbornanyl, [2.2.2]bicycloocatane or [4.4.0]dicyclodecane According to the present disclosure, the "heteroaryl" can be connected to the remaining part of a molecule by the heteroatoms. The aryl or the heteroaryl includes, but is not limited to, phenyl, naphthyl, biphenyl, pyrryl, pyrazolyl, imidazolyl, pyrazinyl, oxazolyl, phenyl-oxazolyl, isoxazolyl, thiazolyl, furyl, thienyl, pyridyl, pyrimidyl, benzothiazolyl, purinyl, benzimidazolyl, indolyl, isoquinolyl, quinoxalinyl, quinolyl, 1-naphthyl, 2-naphthyl, 4-biphenyl, 1-pyrryl, 2-pyrryl, 3-pyrryl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl or 6-quinolyl, and 1, 2, 3 or 4 sites are substituted with substituent groups.

According to the present disclosure, the "isomer" may be a cis-isomer or a trans-isomer, a (−)-enantiomer or a (+)-enantiomer, an (R)-enantiomer or an (S)-enantiomer, a diastereoisomer, a (D)-isomer, a (L)-isomer, or a racemic mixture thereof.

According to the present disclosure, the "active ingredient" refers to a chemical entity, and can treat target disorder, diseases or conditions.

According to the present disclosure, the "and/or" includes one listed item and a combination of any number of items.

According to the present disclosure, the "including" is open description, and denotes coverage of described specified ingredients or steps and other specified ingredients or steps without substantial influence.

According to the present disclosure, the "optionally" denotes that an event or situation described later is possible to appear, but not required, and the description includes a case in which the event or situation occurs and a case in which the event or situation does not occur.

According to the present disclosure, the "treatment" denotes that after a disease has begun to develop, the progress or severity of a type of physical sign, symptom, disorder, condition or disease is retarded, interrupted, prevented, controlled, stopped, relieved or reversed, but it does not necessarily involve complete elimination of related physical signs, symptoms, conditions or disorder of all diseases.

According to the present disclosure, the "or pharmaceutically acceptable salt thereof" refers to a salt prepared from pharmaceutically acceptable non-toxic acid or alkali, wherein the acid or the alkali includes inorganic acid or alkali or organic acid or alkali.

The inorganic acid is selected from hydrochloric acid, hydrobromic acid, phosphoric acid, hydroiodic acid or sulfuric acid. The inorganic alkali is selected from calcium, magnesium, lithium, sodium, zinc, aluminium or potassium. The organic acid is selected from formic acid, glycolic acid, propionic acid, acetic acid, succinic acid, methane sulfonic acid, ethanesulfonic acid, maleic acid, glutamic acid, benzoic acid, stearic acid, alginic acid, benzene sulfonic acid, glucuronic acid, pamoic acid or galacturonic acid. The organic alkali is selected from diethanolamine, choline, procaine, lysine or 1,2-ethylenediamine.

BRIEF DESCRIPTION OF THE DRAWINGS

The embodiments of the present disclosure will be illustrated in detail below in connection with the drawings, wherein:

FIG. 1 shows a structure of a compound in conformity with a general formula I.

DETAILED DESCRIPTION

Clear and full description will be carried out below in connection with the technical solution of the embodiments of the present disclosure. It is obvious that the described embodiments are just a part but not all of the embodiments of the present disclosure. Based on the embodiments of the present disclosure, those of ordinary skill in the art can obtain other embodiment(s), without any inventive work, which should be within the scope of protection of the present disclosure.

Embodiment 1

Preparation steps of a target compound

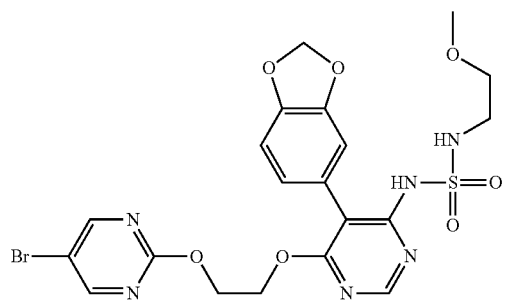 [SMILES: COCCNS(=O)(=O)Nc1ncnc(OCCOc2ncc(Br)cn2)c1-c1ccc2c(c1)OCO2]

X are as follows:

S1, Synthesis of Compound F

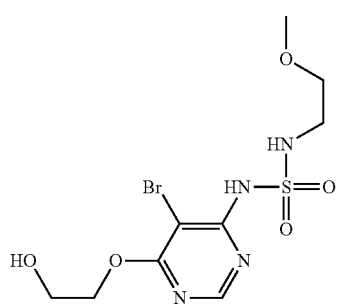

Compound F

1) At the room temperature, a compound A (30.00 g, 211.97 mmol, 18.40 mL) is dissolved in dichloromethane (200 mL), then cooling is carried out to the temperature of 0° C., a dichloromethane (100 mL) solution of tert-butyl alcohol (15.71 g, 211.97 mmol, 20.40 mL) is slowly added (the dropwise adding time is about 1 hour), and a reaction mixture is heated to the room temperature and stirred for 1 hour. A target compound B (a crude product) is reserved in the reaction solvent dichloromethane and directly used for the subsequent reaction.

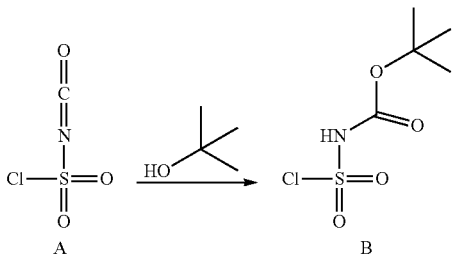

2) At the room temperature, compounds 2-methoxyethylamine (2.00 g, 26.63 mmol, 2.33 mL) and triethylamine (5.39 g, 53.26 mmol, 7.38 mL) are dissolved into dichloromethane (100.00 mL), then a reaction mixture is cooled to the temperature of 0° C., a dichloromethane solution of the compound B (26.63 mmol, the crude product) is slowly added into the above reaction liquid (the dropwise adding time is about 0.5 hour), and the reaction mixture is heated to the room temperature and stirred for 15 hours. After the reaction is finished, the solvent is removed under reduced pressure, water (100 mL) is added into the obtained residue, pH is regulated to 5 by 1M hydrochloric acid, and extraction is carried out by ethyl acetate (100 mL×3). Organic phases are mixed, washing is carried out by a saturated salt solution (100 mL), drying is carried out by anhydrous sodium sulfate, filtering is carried out, and the solvent is removed from the obtained filtrate under reduced pressure so as to obtain a target compound C (white solid, 6.00 g, the yield of 88.59%). 1H NMR (400 MHz, CDCl$_3$) δ: 7.37 (s, 1H) 5.50 (br s, 1H) 3.53 (t, J=5.0 Hz, 2H), 3.40 (s, 3H), 3.26 (d, J=4.8 Hz, 2H) 1.51 (s, 9H).

Compound C

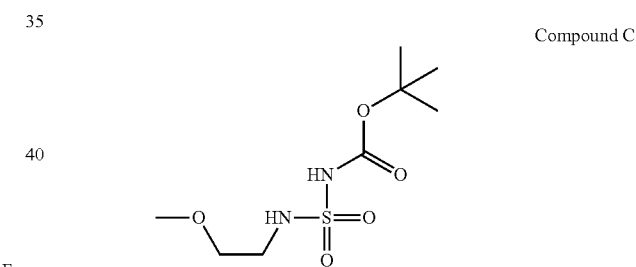

3) At the room temperature, the compound C (6.00 g, 23.59 mmol) is added into water (100.00 mL), and a reaction mixture is heated to the temperature of 100° C. and stirred for 1 hour. After the reaction is finished, cooling is carried out to the room temperature, and extraction is carried out by ethyl acetate (100 mL×3). Organic phases are mixed, washing is carried out by a saturated salt solution (100 mL), drying is carried out by anhydrous sodium sulfate, filtering is carried out, and the solvent is removed from the obtained filtrate under reduced pressure so as to obtain a target compound D (yellow solid, 2.00 g, the yield of 54.99%). 1H NMR (400 MHz, CDCl3) δ: 5.52 (br s, 2H), 3.58-3.48 (m, 2H), 3.41-3.19 (m, 5H).

Compound D

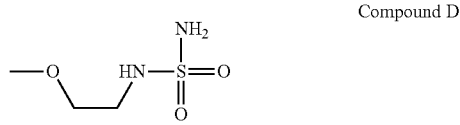

4) At the room temperature, the compound D (1.12 g, 7.24 mmol) and potassium tert-butoxide (2.22 g, 19.75 mmol) are added into dimethyl sulfoxide (20.00 mL), a reaction mixture is stirred for 0.5 hour at the room temperature, then 5-bromo-4,6-dichloropyrimidine (1.50 g, 6.58 mmol) is added into the above reaction liquid, and the reaction mixture is continuously stirred for 6 hours at the room temperature. After the reaction is finished, water (100 mL) is added, pH is regulated to 6 by 1M diluted hydrochloric acid, and extraction is carried out by ethyl acetate (100 mL×3). Organic phases are mixed, washing is carried out by a saturated salt solution (100 mL), drying is carried out by anhydrous sodium sulfate, filtering is carried out, the solvent is removed from the obtained filtrate under reduced pressure, and the obtained residue is subjected to column chromatography (an eluent: a volume ratio of dichloromethane to methyl alcohol is 30:1) separation so as to obtain a target compound E (yellow solid, 1.40 g, the yield of 61.56%). 1H NMR (400 MHz, CDCl3) δ: 8.57 (s, 1H), 7.89 (br s, 1H), 5.99 (br s, 1H), 3.36 (br d, J=2.3 Hz, 2H), 3.32-3.20 (m, 5H).

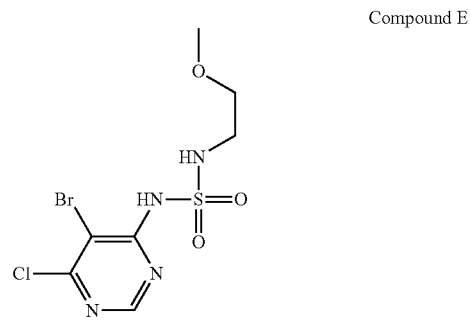 [SMILES: COCCNS(=O)(=O)Nc1ncnc(Cl)c1Br]

Compound E

5) At the room temperature, potassium tert-butoxide (1.36 g, 12.15 mmol) is added into ethylene glycol (22.20 g, 357.66 mmol, 20.00 mL), a reaction mixture is heated to the temperature of 40° C. and stirred for 0.5 hour, then an ethylene glycol dimethyl ether (10.00 mL) solution of the compound E (1.40 g, 4.05 mmol) is added into the above solution, and the reaction mixture is heated to the temperature of 110° C. and continuously stirred for 12 hours. After the reaction is finished, cooling is carried out to the room temperature, water (50 mL) is added, pH is regulated to 3 by 1M diluted hydrochloric acid, and extraction is carried out by ethyl acetate (50 mL×3). Organic phases are mixed, washing is carried out by a saturated salt solution (50 mL), drying is carried out by anhydrous sodium sulfate, filtering is carried out, the solvent is removed from the obtained filtrate under reduced pressure, and the obtained residue is subjected to column chromatography (an eluent: a volume ratio of dichloromethane to methyl alcohol is 20:1) separation so as to obtain the target compound F (yellow solid, 1.20 g, the yield of 76.63%). MS-ESI m/z: 370.8 [M+H]+, 372.8 [M+H]+. 1H NMR (400 MHz, CDCl3) δ: 8.39 (s, 1H), 7.64 (br s, 1H), 6.03-5.94 (m, 1H), 4.65-4.54 (m, 2H), 3.99 (d, J=3.0 Hz, 2H), 3.49 (t, 0.7=5.0 Hz, 2H), 3.33-3.19 (m, 5H), 2.39 (t, J=5.3 Hz, 1H).

S2: Synthesis of Compound H

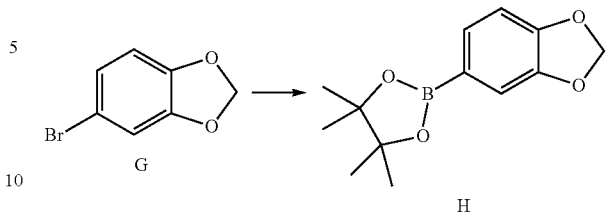

At the room temperature, a compound G (3.00 g, 14.92 mmol), bis(pinacolato)diboron (7.58 g, 29.84 mmol) and potassium acetate (4.39 g, 44.76 mmol) are added into 1,4-dioxane (30.00 mL), then [1,1'-bis(diphenylphosphino)ferrocene]dichloropalladium (3.28 g, 4.48 mmol) is added, and under the protection of nitrogen gas, a reaction mixture is heated to the temperature of 80° C. and stirred for 16 hours. After the reaction is finished, cooling is carried out to the room temperature, filtering is carried out, the solvent is removed from the obtained filtrate under reduced pressure, water (30 mL) is added into the obtained residue, and extraction is carried out by ethyl acetate (20 mL×3). Organic phases are mixed, and drying is carried out by anhydrous sodium sulfate. Filtering is carried out, the solvent is removed from the obtained filtrate under reduced pressure, and the obtained residue is subjected to column chromatography (an eluent: a volume ratio of petroleum ether to ethyl acetate is 1:0 to 100:1) separation so as to obtain the target compound H. 1H NMR (400 MHz, CDCl3) δ: 7.38 (dd, 0.7=7.8, 0.8 Hz, 1H), 7.26 (s, 1H), 6.85 (d, J=7.8 Hz, 1H), 5.97 (s, 2H), 1.35 (s, 12H).

S3: Synthesis of Compound I

At the room temperature, the compound F (300.00 mg), the compound H (419.04 mg) and potassium phosphate (537.83 mg, 2.53 mmol) are added into N,N-dimethylformamide (20.00 mL), then [1,1'-bis(diphenylphosphino)ferrocene]dichloropalladium (185.39 g, 253.37 μmol) is added, and under the protection of nitrogen gas, a reaction mixture is heated to the temperature of 80° C. and stirred for 16 hours. After the reaction is finished, cooling is carried out to the room temperature, water (100 mL) is added, extraction is carried out by ethyl acetate (20 mL×1), and an organic phase is discarded. pH of a water phase is regulated to 5 to 6 by 3M diluted hydrochloric acid, and extraction is carried out by ethyl acetate (20 mL×3). The organic phases are mixed, drying is carried out by anhydrous sodium sulfate, filtering is carried out, the solvent is removed from the obtained filtrate under reduced pressure, and the obtained residue is subjected to preparative chromatography plate (an eluent: a volume ratio of petroleum ether to ethyl acetate is 1:2) separation so as to obtain the compound I.

S4: Synthesis of Compound X

At the room temperature, sodium hydride (145.30 mg, 3.63 mmol, the purity of 60%) is added into anhydrous tetrahydrofuran (20 mL), then an anhydrous N,N-dimethylformamide (1 mL) solution of the compound I (180.00 mg, 454.06 μmol) and an anhydrous tetrahydrofuran (1 mL) solution of 5-bromo-2-chloropyrimidine (175.66 mg, 908.13 μmol) are respectively added, and under the protection of nitrogen gas, a reaction mixture is heated to the temperature of 70° C. and stirred for 2 hours.

After the reaction is finished, cooling is carried out to the room temperature, a saturated ammonium chloride solution (30 mL) is added, pH is regulated to 4 to 5 by 1M diluted hydrochloric acid, and extraction is carried out by ethyl acetate (20 mL×3). Organic phases are mixed, washing is carried out by a saturated salt solution (50 mL), drying is carried out by anhydrous sodium sulfate, filtering is carried out, the solvent is removed from the obtained filtrate under reduced pressure, and the obtained residue is subjected to preparative high performance liquid chromatography (HPLC) separation so as to obtain the target compound X. $^1$H NMR (400 MHz, CDCl$_3$) δ: 8.49 (s, 2H), 8.46 (s, 1H), 6.97 (s, 1H), 6.79 (d, J=8.3 Hz, 1H), 6.68-6.43 (m, 2H), 6.02-5.91 (m, 3H), 4.71-4.61 (m, 2H), 4.60-4.52 (m, 2H), 3.42 (t, J=5.0 Hz, 2H), 3.22 (s, 3H), 3.13-3.01 (M, 2H). Liquid chromatography mass spectrometry (LCMS) data is that MS-ESI m/z: 569.0 [M+H]+, 571.0 [M+H+2]+.

Embodiment 2

I Material and Method

1. Experimental Animals and Feeding 40 healthy SD rats (180-220 g, male) are purchased from Beijing Vital River Laboratory Animal Technology Co. Ltd, belong to the SPF grade and have the license number of SCXK(Jing)2016-0006. The healthy SD rats are fed in a low-pressure oxygen cabin, and regularly fed with a complete nutritional feed under the conditions of the temperature of 22 to 25° C. and the humidity of 30% to 50%.

2. Reagents and Sample Groups

SC0062 is the compound X prepared in Embodiment 1 of the present disclosure; Solutol is purchased from Beijing Taize Jiaye Technology Development Co., Ltd.; HP-β-CD is purchased from solaxbio, with the specification of 25 mg per pack and CAS of 128446-35-5;

Solvent configuration: 5% of DMSO and 95% of normal saline with 10% of HP-β-CD, and pH=9.

Groups:

A blank control group: normal-pressure normal-oxygen feeding

A model group: a low-pressure low-oxygen cabin, and intragastric administration of a solvent An experimental group A: a low-pressure low-oxygen cabin, and intragastric administration of sc0062 (15 mg/kg) as well as a solvent An experimental group B: a low-pressure low-oxygen cabin, and intragastric administration of sc0062 (30 mg/kg) as well as a solvent 3. Instruments A multi-factor composite environment simulated medical science experiment module (the type of DYC-3285, the Instrument Center of the Beijing Military Medical Science Academy);

A small animal breathing machine (kent scientific, the United States);

A multifunctional physiograph (Millar, the United States);

A full-automatic animal blood cell analysis meter (Mindray Co., Ltd); and

A small animal ultrasonic instrument (Visual Sonics Inc, Canada).

4. Experiment Design and Process 40 rats are randomly divided into four groups, each group includes 10 rats, 3 groups are placed into a low-pressure low-oxygen cabin, the pressure of the oxygen cabin is regulated to 380 mmHg, a high altitude environment with an altitude of 5,500 meters is simulated, the low-pressure low-oxygen cabin is opened for 1 hour every day so as to add foods and water for animals and carry out corresponding medicine treatment, and meanwhile, the environment where the rats are positioned are kept alternate day and night according to a ratio of 12 h:12 h. After 3 groups of rats are in the oxygen-poor environment for 14 days, intragastric administration is respectively carried out on the 3 groups of rats, the solvent (the model group), the sc0062 (15 mg/kg) and the solvent (the experimental group A) and the sc0062 (30 mg/kg) and the solvent (the experimental group B) are respectively applied to the 3 groups of rats, and the operation is continued for 14 days. Rats in the fourth group (the blank control group) are placed in the same room to be fed in the normal-pressure normal-oxygen environment.

5. Index Detection Method

3% pentobarbital sodium (0.2 mL/100 g) is intraperitoneally injected to anesthetize the rats, ultrasonic detection is carried out, and the following ultrasonic data is recorded: PAT/PET (pulmonary arterial blood flow acceleration time/ right ventricular pre-ejection period); right ventricular ejection fraction EF; a right ventricular fractional shortening FS; and tricuspid annular plane systolic excursion TAPSE. The anesthetize rats are fixed on an operating table in a supine position mode, tracheotomy is carried out, a breathing machine is connected, and thoracotomy is carried out to expose the hearts. A catheter is inserted into each right ventricle, and the right ventricular systolic pressure is recorded. Then each catheter is slowly pushed forwards, can reach a corresponding pulmonary artery through a corresponding right ventricular outflow tract, the pressure waveform of a monitor is observed, and the mean pulmonary arterial pressure mPAP is recorded. Blood is collected and the rats are executed. The hearts and the lung tissue are taken out, the atrial tissue and the root of the main artery are removed, left and right ventricles are separated, bloodstain is washed out in PBS, moisture is sucked up by filter paper, and the weight of the right ventricles (RV) and the weight of the left ventricles and the atrioventricular septum (LV+IS) are respectively weighed. Calculation is carried out according to the following formula: right ventricular hypertrophy index=RV/(LV+IS).

6. Statistical Method

All the data is represented by x±s, comparison among the groups is single factor analysis of variance, when P<0.05, it represents that the difference has a statistical significance, and statistical treatment is carried out by adopting an SPSS 22.0 software package.

II Experimental Result

1. Influence on Rat Echocardiography

The right ventricular function of the model group (the solvent group) in the low-pressure low-oxygen cabin is obviously reduced, and has the obvious difference from that of the blank control group. The EF value, the FS value and the TAPSE value are significantly reduced (p<0.01), the PAT/PET value is reduced, and both of them have the statistic differences (p<0.05). Compared with the model group, the experimental group A and the experimental group B are remarkably improved in EF value and FS value and are obviously increased in TAPSE value and PAT/PET value, and the specific data are as shown in Table 1.

TABLE 1

Changes of parameters EF, FS, TAPSE and PAT/PET after echocardiography on each group of rats

| Groups | Right ventricular EF | Right ventricular FS | PAT/PET | TAPSE |
|---|---|---|---|---|
| Blank control group | 80.61 ± 6.65 | 48.3 ± 6.96 | 0.39 ± 0.08 | 3.05 ± 0.71 |
| Model group | 50.51 ± 13.51 | 25.13 ± 8.28 | 0.35 ± 0.05 | 1.66 ± 0.31 |
| A: sc0062 (15 mg/kg) | 67.25 ± 13.01 | 37.02 ± 10.63 | 0.39 ± 0.07 | 2.05 ± 0.29 |
| B: sc0062 (30 mg/kg) | 71.32 ± 9.35 | 39.76 ± 7.24 | 0.40 ± 0.07 | 1.93 ± 0.44 |

2. Influence on Rat Haemodynamics

The mean pulmonary arterial pressure of the model group (the solvent group) in the low-pressure low-oxygen cabin is obviously raised, and has the significant difference (p<0.01) from that of the blank control group. Compared with the mean pulmonary arterial pressure of the model group, the mean pulmonary arterial pressures of the SC0062 treatment groups (the experimental groups A and B) are significantly raised (p<0.01), and the specific data is as shown in Table 2.

TABLE 2

Influence of compounds prepared in Embodiment 1 of the present disclosure on pulmonary arterial hypertension of model rats

| Groups | mPVP |
|---|---|
| Blank control group | 14.35 ± 3.41 |
| Model group | 36.63 ± 3.03 |
| Experimental group A: sc0062 (15 mg/kg) | 31.39 ± 3.90 |
| Experimental group B: sc0062 (30 mg/kg) | 26.91 ± 4.35 |

3. Influence on Rat Right Ventricular Hypertrophy

The right ventricular hypertrophy index of the model group (the solvent group) in the low-pressure low-oxygen cabin is obviously increased, and has the significant difference (p<0.01) from that of the blank control group. Compared with the right ventricular hypertrophy index of the model group, the right ventricular hypertrophy indexes of the SC0062 groups (the experimental groups A and B) are reduced, there is a statistic difference (p<0.05), and the specific data is as shown in Table 3.

TABLE 3

Change situations of right ventricular hypertrophy indexes of each group of rats

| Groups | RV | Full heart | RV/(LV + IS) |
|---|---|---|---|
| Blank control group | 0.27 ± 0.02 | 1.22 ± 0.08 | 0.28 ± 0.04 |
| Model group | 0.57 ± 0.81 | 1.38 ± 0.20 | 0.71 ± 0.15 |
| Experimental group A: sc0062 (15 mg/kg) | 0.56 ± 0.09 | 1.47 ± 0.24 | 0.38 ± 0.02 |
| Experimental group B: sc0062 (30 mg/kg) | 0.48 ± 0.11 | 1.30 ± 0.21 | 0.36 ± 0.02 |

From the above, the compound provided by the present disclosure has treatment and/or prevention effects on the high altitude disease generated in the high altitude low-pressure low-oxygen environment, particularly has the very strong protection effect on the heart and the lung in the high altitude low-pressure low-oxygen environment, and can be developed into a medicament for preventing and treating the high altitude disease.

The preferred embodiments of the present disclosure are described in detail above, but the present disclosure is not limited to the specific details in the above-mentioned embodiments. Various simple modifications can be made to the technical solution of the present disclosure within the scope of the technical concept of the present disclosure, and those simple modifications all shall fall within the scope of protection of the present disclosure.

In addition, it should be noted that each specific technical characteristic described in the specific embodiments, without conflict, can be combined in any proper mode, and in order to avoid unnecessary repetition, various possible combination modes will not be additionally illustrated in the present disclosure.

The invention claimed is:

1. A method for treating or preventing a high altitude disease with a medicinal composition, comprising:
    administering a therapeutically effective amount of a compound in conformity with a general formula I and an isomer or pharmaceutically acceptable salt thereof,

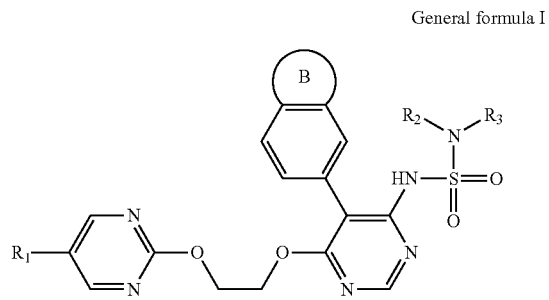

General formula I wherein
$R_1$ is selected from H, F, Cl, Br, I, OH or $NH_2$;
$R_2$ is selected from H or $C_{1-3}$ alkyl, and the $C_{1-3}$ alkyl is optionally substituted with 1, 2 or 3 X;
$R_3$ is selected from H, $C_{1-6}$ alkyl, $C_{1-6}$ heteroalkyl, $-C_{1-3}$ alkyl-$C_{3-6}$ cycloalkyl, $C_{3-6}$ cycloalkyl and $-C_{1-3}$ alkyl-3- to 7-membered heterocycloalkyl, and the $C_{1-6}$ alkyl, the $C_{1-6}$ heteroalkyl, the $-C_{1-3}$ alkyl-$C_{3-6}$ cycloalkyl, the $C_{3-6}$ cycloalkyl or the $-C_{1-3}$ alkyl-3- to 7-membered heterocycloalkyl is optionally substituted with 1, 2 or 3 X;
or, $R_2$ and $R_3$ are connected to form a 3- to 8-membered ring optionally substituted with 1, 2 or 3 X;
a ring B is selected from 3- to 7-membered heterocycloalkyl or 5-6-membered heteroaryl, and the 3- to 7-membered heterocycloalkyl or the 5-6-membered heteroaryl is optionally substituted with 1, 2 or 3 X;

X is respectively and independently selected from H, F, Cl, Br, I, OH, NH$_2$, CN, C$_{1-6}$ alkyl or C$_{1-6}$ heteroalkyl, and the C$_{1-6}$ alkyl or the C$_{1-6}$ heteroalkyl is optionally substituted with 1, 2 or 3 X';

X' is respectively and independently selected from F, Cl, Br, I, OH, NH$_2$, CN, Me, CH$_2$F, CHF$_2$, CF$_3$ and Et; and the C$_{1-6}$ heteroalkyl, the 3- to 7-membered heterocycloalkyl and the 5-6-membered heteroaryl each comprise 1, 2, 3 or 4 heteroatoms or heteroatom groups independently selected from N, —O—, —S—, —NH—, —S(=O)$_2$- or —S(=O)—.

2. The method of claim 1, wherein the X is selected from H, F, Cl, Br, I, OH, NH$_2$, CN, Me, CH$_2$F, CHF$_2$, CF$_3$, Et,

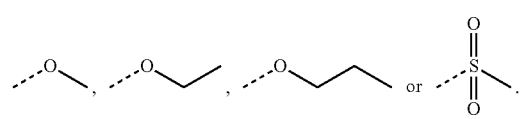

3. The method of claim 1, wherein the ring B is selected from tetrahydrofuryl, tetrahydrothienyl, 1,3-dioxolanyl, pyrrolidyl, thiazolyl, pyrazolyl or imidazolyl, and the tetrahydrofuryl, the tetrahydrothienyl, the 1,3-dioxolanyl, the pyrrolidyl, the thiazolyl, the pyrazolyl or the imidazolyl is optionally substituted with 1, 2 or 3 X.

4. The method of claim 1, wherein the R$_3$ is selected from H or Me.

5. The method of claim 1, wherein the R$_3$ is selected from H, Me, Et,

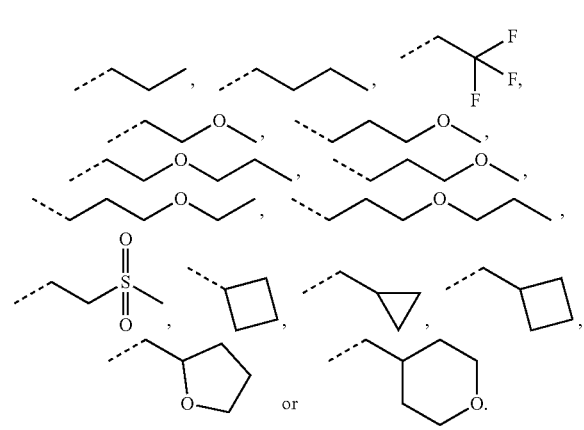

6. The method of claim 1, wherein the R$_2$ and the R$_3$ are connected to form 6- to 8-membered heterocycloalkyl, and the obtained 6- to 8-membered heterocycloalkyl is optionally substituted with 1, 2 or 3 X.

7. The method of claim 1, wherein the R$_1$ is selected from H, F, Cl, Br, I, OH or NH$_2$; the X is selected from H, F, Cl, Br, I, OH, NH$_2$, CN, Me, CH$_2$F CHF$_2$, CF$_3$, Et,

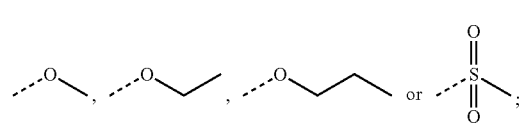;

the ring B is selected from tetrahydrofuryl, tetrahydrothienyl, 1,3-dioxolanyl, pyrrolidyl, thiazolyl, pyrazolyl or imidazolyl, and the tetrahydrofuryl, the tetrahydrothienyl, the 1,3-dioxolanyl, the pyrrolidyl, the thiazolyl, the pyrazolyl or the imidazolyl is optionally substituted with 1, 2 or 3 X; the R$_2$ is selected from H or Me; and the R$_3$ is selected from H, Me, Et,

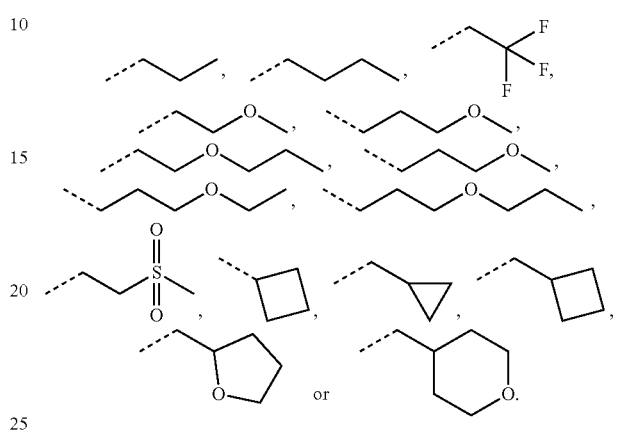

8. The method of claim 1, wherein the compound as shown in the general formula I is SC0062, and a structural formula of the SC0062 is as follows:

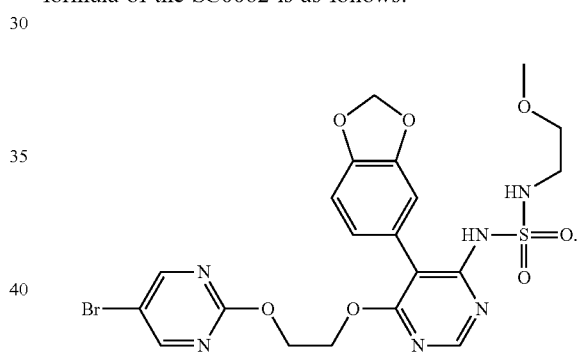

9. The method of claim 1, wherein the high altitude disease is selected from an acute high altitude disease and a chronic high altitude disease generated in a high altitude environment.

10. The method of claim 9, wherein the acute high altitude disease is selected from high altitude coma, high altitude cerebral edema, high altitude pulmonary edema or a mixed disease with coexistence of cerebral and pulmonary abnormality symptoms; and/or the chronic high altitude disease is selected from a high altitude heart disease, high altitude polycythemia, high altitude hypertension, high altitude hypotention or a mixed disease with coexistence of the heart disease and the polycythemia.

11. The method of claim 1, wherein the medicinal composition comprises the compound which is used as an active ingredient and has the general formula I, the isomer or the pharmaceutically acceptable salt of the compound, and a medicinal auxiliary material.

* * * * *